(12) United States Patent
Baird et al.

(10) Patent No.: US 8,192,490 B2
(45) Date of Patent: Jun. 5, 2012

(54) METHODS AND SYSTEMS FOR MATERIAL FIXATION

(75) Inventors: Kevin N. Baird, Phoenix, AZ (US);
Derek J. Harper, Prescott, AZ (US); Joe P. Kovalski, Ventura, CA (US); Joanne Kovalski, legal representative, Ventura, CA (US); Kenneth D. Montgomery, Roslyn, NY (US)

(73) Assignee: Cayenne Medical, Inc., Scottsdale, AZ (US)

( * ) Notice: Subject to any disclaimer, the term of this patent is extended or adjusted under 35 U.S.C. 154(b) by 0 days.

(21) Appl. No.: 13/014,469

(22) Filed: Jan. 26, 2011

(65) Prior Publication Data

US 2011/0184517 A1  Jul. 28, 2011

Related U.S. Application Data

(62) Division of application No. 11/923,526, filed on Oct. 24, 2007, now Pat. No. 7,879,094.

(51) Int. Cl.
*A61F 2/08* (2006.01)
*F16B 13/04* (2006.01)
*A61B 17/04* (2006.01)

(52) U.S. Cl. ............... 623/13.14; 623/13.11; 623/13.12; 606/62; 606/300; 411/32

(58) Field of Classification Search .... 623/13.11–13.14, 623/16.11; 606/60, 62–65, 88, 232, 236, 606/300, 310; 411/16
See application file for complete search history.

(56) References Cited

U.S. PATENT DOCUMENTS

| | | | |
|---|---|---|---|
| 3,708,883 A | 1/1973 | Flander | |
| 3,832,931 A | 9/1974 | Talan | |
| 4,311,421 A | 1/1982 | Okada et al. | |
| 4,711,232 A | 12/1987 | Fischer et al. | |

(Continued)

FOREIGN PATENT DOCUMENTS

CA  2235354 A1  10/1999

(Continued)

OTHER PUBLICATIONS

Caborn et al., A Biomechanical Comparison of Initial Soft Tissue Tibial Fixation Devices: The Intrafix Versus a Tapered 35-mm Bioabsorbable Interference Screw, The American Journal of Sports Medicine, 2004, vol. 32, No. 4.

(Continued)

*Primary Examiner* — David Isabella
*Assistant Examiner* — Yashita Sharma
(74) *Attorney, Agent, or Firm* — Stout, Uxa, Buyan & Mullins, LLP; Donald E. Stout

(57) ABSTRACT

A soft tissue fixation system, most typically applicable to orthopedic joint repairs, such as anterior cruciate ligament (ACL) knee repair procedures, comprises an implant which is placeable in a tunnel disposed in a portion of bone, wherein the tunnel is defined by walls comprised of bone. A first member is deployable outwardly to engage the tunnel walls for anchoring the implant in place in the tunnel, and a second member is deployable outwardly to engage tissue material to be fixed within the tunnel. The second member also functions to move the tissue material outwardly into contact with the tunnel walls to promote tendon-bone fixation. Extra graft length is eliminated by compression of the tendon against the bone at the aperture of the femoral tunnel, which more closely replicates the native ACL and increases graft stiffness. The inventive device provides high fixation of tendon to bone and active tendon-bone compression. Graft strength has been found to be greater than 1,000 N (Newtons), which is desirable for ACL reconstruction systems.

15 Claims, 15 Drawing Sheets

U.S. PATENT DOCUMENTS

| | | |
|---|---|---|
| 4,716,893 A | 1/1988 | Fischer et al. |
| 4,738,255 A | 4/1988 | Goble et al. |
| 4,744,793 A | 5/1988 | Parr et al. |
| 4,772,286 A | 9/1988 | Goble et al. |
| 4,778,468 A | 10/1988 | Hunt et al. |
| 4,828,562 A | 5/1989 | Kenna |
| 4,870,957 A | 10/1989 | Goble et al. |
| 4,955,910 A | 9/1990 | Bolesky |
| 4,957,498 A | 9/1990 | Caspari et al. |
| 5,004,474 A | 4/1991 | Fronk et al. |
| 5,037,422 A | 8/1991 | Hayhurst et al. |
| 5,085,661 A | 2/1992 | Moss |
| 5,139,520 A | 8/1992 | Rosenberg |
| 5,161,916 A | 11/1992 | White et al. |
| 5,176,709 A | 1/1993 | Branemark |
| 5,188,636 A | 2/1993 | Fedotov |
| 5,211,647 A | 5/1993 | Schmieding |
| 5,234,430 A | 8/1993 | Huebner |
| 5,236,445 A | 8/1993 | Hayhurst et al. |
| 5,258,016 A | 11/1993 | DiPoto et al. |
| 5,268,001 A | 12/1993 | Nicholson et al. |
| 5,281,237 A | 1/1994 | Gimpelson |
| 5,320,626 A | 6/1994 | Schmieding |
| 5,336,240 A | 8/1994 | Metzler et al. |
| 5,350,383 A | 9/1994 | Schmieding et al. |
| 5,354,298 A | 10/1994 | Lee et al. |
| 5,356,435 A | 10/1994 | Thein |
| 5,374,269 A | 12/1994 | Rosenberg |
| 5,383,878 A | 1/1995 | Roger et al. |
| 5,411,523 A | 5/1995 | Goble |
| 5,431,651 A | 7/1995 | Goble |
| 5,431,666 A | 7/1995 | Sauer et al. |
| 5,439,467 A | 8/1995 | Benderev et al. |
| 5,456,685 A | 10/1995 | Huebner |
| 5,464,427 A | 11/1995 | Curtis et al. |
| 5,466,237 A | 11/1995 | Byrd et al. |
| 5,474,555 A | 12/1995 | Puno et al. |
| 5,480,403 A | 1/1996 | Lee et al. |
| 5,486,197 A | 1/1996 | Le et al. |
| 5,507,750 A | 4/1996 | Goble et al. |
| 5,571,104 A | 11/1996 | Li |
| 5,571,184 A | 11/1996 | DeSatnick |
| 5,575,819 A | 11/1996 | Amis |
| 5,601,562 A | 2/1997 | Wolf et al. |
| 5,603,716 A | 2/1997 | Morgan et al. |
| 5,618,314 A | 4/1997 | Harwin et al. |
| 5,632,748 A | 5/1997 | Beck, Jr. et al. |
| 5,645,589 A | 7/1997 | Li |
| 5,702,215 A | 12/1997 | Li |
| 5,702,397 A | 12/1997 | Goble et al. |
| 5,707,395 A | 1/1998 | Li |
| 5,713,903 A | 2/1998 | Sander et al. |
| 5,718,706 A | 2/1998 | Roger |
| 5,725,341 A | 3/1998 | Hofmeister |
| 5,725,529 A | 3/1998 | Nicholson et al. |
| 5,725,541 A | 3/1998 | Anspach, III et al. |
| 5,728,136 A | 3/1998 | Thal |
| 5,741,300 A | 4/1998 | Li |
| 5,743,912 A | 4/1998 | Lahille et al. |
| 5,769,894 A | 6/1998 | Ferragamo |
| 5,782,865 A | 7/1998 | Grotz |
| 5,814,073 A | 9/1998 | Bonutti |
| 5,845,645 A | 12/1998 | Bonutti |
| 5,846,254 A | 12/1998 | Schulze et al. |
| 5,871,504 A | 2/1999 | Eaton et al. |
| 5,899,938 A | 5/1999 | Sklar et al. |
| 5,902,303 A | 5/1999 | Eckhoff et al. |
| 5,911,721 A | 6/1999 | Nicholson et al. |
| RE36,289 E | 8/1999 | Le et al. |
| 5,931,869 A | 8/1999 | Boucher et al. |
| 5,935,129 A | 8/1999 | McDevitt et al. |
| 5,941,901 A | 8/1999 | Egan |
| 5,957,953 A | 9/1999 | DiPoto et al. |
| 5,961,520 A | 10/1999 | Beck, Jr. et al. |
| 5,964,764 A | 10/1999 | West, Jr. et al. |
| 5,968,078 A | 10/1999 | Grotz |
| 5,993,459 A | 11/1999 | Larsen et al. |
| 6,017,346 A | 1/2000 | Grotz |
| 6,086,608 A | 7/2000 | Ek et al. |
| 6,099,530 A | 8/2000 | Simonian et al. |
| 6,113,609 A | 9/2000 | Adams |
| 6,117,173 A | 9/2000 | Taddia et al. |
| 6,132,433 A | 10/2000 | Whelan |
| 6,146,406 A | 11/2000 | Shiuzas et al. |
| 6,152,928 A | 11/2000 | Wenstrom, Jr. |
| 6,179,840 B1 | 1/2001 | Bowman |
| 6,187,008 B1 | 2/2001 | Hamman |
| 6,190,411 B1 | 2/2001 | Lo |
| 6,214,007 B1 | 4/2001 | Anderson |
| 6,221,107 B1 | 4/2001 | Steiner et al. |
| 6,325,804 B1 | 12/2001 | Wenstrom, Jr. et al. |
| 6,328,758 B1 | 12/2001 | Tornier et al. |
| 6,355,066 B1 | 3/2002 | Kim |
| 6,379,361 B1 | 4/2002 | Beck, Jr. et al. |
| 6,387,129 B2 | 5/2002 | Rieser et al. |
| 6,461,373 B2 | 10/2002 | Wyman et al. |
| 6,482,210 B1 | 11/2002 | Skiba et al. |
| 6,517,579 B1 | 2/2003 | Paulos et al. |
| 6,533,795 B1 | 3/2003 | Tran et al. |
| 6,533,816 B2 | 3/2003 | Sklar |
| 6,551,330 B1 | 4/2003 | Bain et al. |
| 6,554,862 B2 | 4/2003 | Hays et al. |
| 6,562,071 B2 | 5/2003 | Jarvinen |
| 6,575,973 B1 | 6/2003 | Shekalim |
| 6,616,694 B1 | 9/2003 | Hart |
| 6,623,524 B2 | 9/2003 | Schmieding |
| 6,632,245 B2 | 10/2003 | Kim |
| 6,648,890 B2 | 11/2003 | Culbert et al. |
| 6,656,183 B2 | 12/2003 | Colleran et al. |
| 6,685,706 B2 | 2/2004 | Padget et al. |
| 6,689,135 B2 * | 2/2004 | Enayati .................. 606/326 |
| 6,716,234 B2 | 4/2004 | Grafton et al. |
| 6,719,509 B1 | 4/2004 | Huang et al. |
| 6,730,124 B2 | 5/2004 | Steiner |
| 6,736,829 B1 | 5/2004 | Li et al. |
| 6,736,847 B2 | 5/2004 | Seyr et al. |
| 6,752,831 B2 | 6/2004 | Sybert et al. |
| 6,770,073 B2 | 8/2004 | McDevitt et al. |
| 6,770,084 B1 | 8/2004 | Bain et al. |
| 6,780,188 B2 | 8/2004 | Clark et al. |
| 6,796,977 B2 | 9/2004 | Yap et al. |
| 6,802,862 B1 | 10/2004 | Roger et al. |
| 6,833,005 B1 | 12/2004 | Mantas et al. |
| 6,887,271 B2 | 5/2005 | Justin et al. |
| 6,890,354 B2 | 5/2005 | Steiner et al. |
| 6,932,841 B2 | 8/2005 | Sklar et al. |
| 6,939,379 B2 | 9/2005 | Sklar |
| 6,942,666 B2 | 9/2005 | Overaker et al. |
| 6,942,668 B2 | 9/2005 | Padget et al. |
| 6,986,781 B2 | 1/2006 | Smith |
| 7,008,451 B2 | 3/2006 | Justin et al. |
| 7,037,324 B2 | 5/2006 | Martinek |
| 7,083,638 B2 | 8/2006 | Foerster |
| 7,147,651 B2 | 12/2006 | Morrison et al. |
| 7,201,754 B2 | 4/2007 | Stewart et al. |
| 7,309,355 B2 | 12/2007 | Donnelly et al. |
| 7,326,247 B2 | 2/2008 | Schmieding et al. |
| 7,556,629 B2 | 7/2009 | Von Hoffmann et al. |
| 7,556,640 B2 | 7/2009 | Foerster |
| 2002/0120280 A1 | 8/2002 | Wotton, III |
| 2002/0165611 A1 | 11/2002 | Enzerink et al. |
| 2003/0065391 A1 | 4/2003 | Re et al. |
| 2003/0083662 A1 | 5/2003 | Middleton |
| 2003/0109900 A1 | 6/2003 | Martinek |
| 2003/0135274 A1 | 7/2003 | Hays et al. |
| 2003/0199877 A1 | 10/2003 | Steiger et al. |
| 2003/0204204 A1 | 10/2003 | Bonutti |
| 2004/0024456 A1 | 2/2004 | Brown, Jr. et al. |
| 2004/0068267 A1 | 4/2004 | Harvie et al. |
| 2004/0097943 A1 | 5/2004 | Hart |
| 2004/0098050 A1 | 5/2004 | Foerster et al. |
| 2004/0098052 A1 | 5/2004 | West, Jr. et al. |
| 2004/0153153 A1 | 8/2004 | Elson et al. |
| 2004/0180308 A1 | 9/2004 | Ebi et al. |
| 2004/0181240 A1 | 9/2004 | Tseng et al. |
| 2004/0199165 A1 | 10/2004 | Culbert et al. |
| 2004/0230194 A1 | 11/2004 | Urbanski et al. |

| | | | |
|---|---|---|---|
| 2004/0237362 | A1 | 12/2004 | O'Connell |
| 2004/0267362 | A1 | 12/2004 | Hwang et al. |
| 2005/0033289 | A1 | 2/2005 | Warren et al. |
| 2005/0251260 | A1 | 11/2005 | Gerber et al. |
| 2006/0095131 | A1 | 5/2006 | Justin et al. |
| 2006/0155287 | A1 | 7/2006 | Montgomery et al. |
| 2008/0119929 | A1 | 5/2008 | Schmieding et al. |

FOREIGN PATENT DOCUMENTS

| | | |
|---|---|---|
| EP | 0232049 B1 | 3/1990 |
| EP | 0528573 A1 | 8/1992 |
| EP | 0688185 A1 | 2/1993 |
| EP | 1033115 A2 | 9/2000 |
| EP | 0762850 B1 | 2/2004 |
| EP | 0739185 B1 | 9/2004 |
| EP | 1011535 B1 | 12/2005 |
| FR | 2696925 A1 | 4/1994 |
| JP | 10155820 A | 6/1998 |
| WO | 8809157 | 12/1988 |
| WO | 9216167 A1 | 10/1992 |
| WO | 9515726 A1 | 6/1995 |
| WO | 9812991 A1 | 4/1998 |
| WO | 9818409 | 5/1998 |
| WO | 0130253 A1 | 5/2001 |
| WO | WO02/085256 A1 | 10/2002 |

OTHER PUBLICATIONS

Charlton et al., Clinical Outcome of Anterior Cruciate Ligament Reconstruction with Quadrupled Hamstring Tendon Graft and Bioabsorbable Interference Screw Fixation, The American Journal of Sports Medicine, 2003, pp. 518-521, vol. 31, No. 4, Kerlan-Jobe Orthopaedic Clinic, Los Angeles.

Morgan et al., Anatomic Graft Fixation Using a Retrograde Biointerference Screw for Endoscopic Anterior Cruciate Ligament Reconstruction: Single-Bundle and 2-Bundle Techniques, Techniques in Orthopaedics, 2005, pp. 297-302, vol. 20, No. 3, Lippincott Williams & Wilkins, Inc., Philadelphia.

Robbe et al., Graft Fixation alternatives in Anterior Cruciate Ligament Reconstruction, Spring 2002, pp. 21-28, vol. 15, Orthopaedic Surgery Department, University of Kentucky School of Medicine, Lexington, KY, U.S.A.

Scheffler et al., Biomechanical Comparison of Hamstring and Patellar Tendon Graft Anterior Cruciate Ligament Reconstruction Techniques: The Impact of Fixation Level and Fixation Method Under cyclic Loading, Arthroscopy: The Journal of Arthroscopic and Related Surgery, Mar. 2002, pp. 304-315, vol. 18, No. 3, Arthroscopy Association of North America.

Simonian et al., Interference Screw Position and Hamstring Graft Location for Anterior Cruciate Ligament Reconstruction, The Journal of Arthroscopic and Related Surgery, Jul.-Aug. 1998, pp. 459-464, vol. 14, No. 5, The New York Hospital—Cornell University Medical College, New York, U.S.A.

Wolf, Eugene M., Hamstring Anterior Cruciate Ligament, Reconstruction using Femoral Cross-pin Fixation, Operative Techniques in Sports Medicine, Oct. 1999, pp. 241-222, vol. 7, No. 4, W.B. Saunders Company, San Francisco, U.S.A.

A Biomechanical Comparison of Femoral RetroScrew Placement in a Porcine Model, Arthrex Research and Development, 2007, Arthex, Inc.

Scope This Out: A Technical Pearls Newsletter for Arthroscopists, Fall 1999, vol. 1, No. 3, Arthrex, Inc, U.S.A.

Scope This Out: A Technical Pearls Newsletter for Arthroscopists, Summer 2001, vol. 3, No. 2, Arthrex, Inc, U.S.A.

Scope This Out: A Technical Pearls Newsletter for Arthroscopists, Summer 2002, vol. 4, No. 2, Arthrex, Inc, U.S.A.

Scope This Out: A Technical Pearls Newsletter for Arthroscopists, Summer 2002, vol. 5, No. 2, Arthrex, Inc, U.S.A.

* cited by examiner

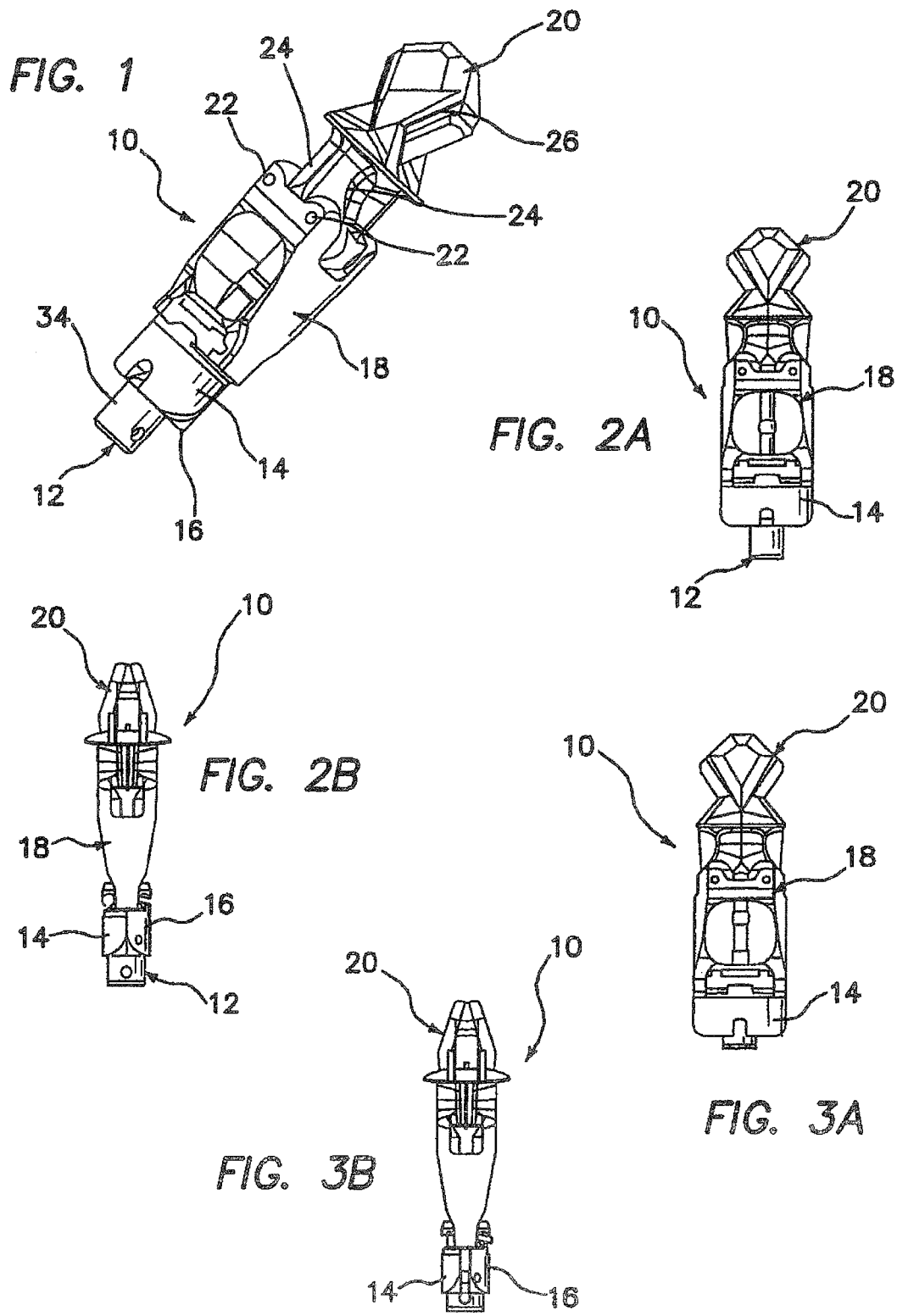

|  |  | Pull out Forces (N) |
|---|---|---|
| Implants | Mean | 1253 |
| | Standard Deviation | 142.5 |
| | Minimum Value | 938.3 |
| | Maximum value | 1567.9 |
|  |  | Pull out Forces (N) |
| RCI Screws | Mean | 532.7 |
| | Standard Deviation | 349.7 |
| | Minimum Value | 135.7 |
| | Maximum value | 1230.9 |

*FIG. 17*

|  | | Pull out Forces (N) |
|---|---|---|
| Cancelous Implant | Mean | 1164.2 |
| | Standard Deviation | 215.9 |
| | Minimum Value | 728 |
| | Maximum Value | 1643 |
|  | | Pull out Forces (N) |
|---|---|---|
| RCI Screws | Mean | 532.7 |
| | Standard Deviation | 349.7 |
| | Minimum Value | 135.7 |
| | Maximum Value | 1230.9 |
FIG. 32
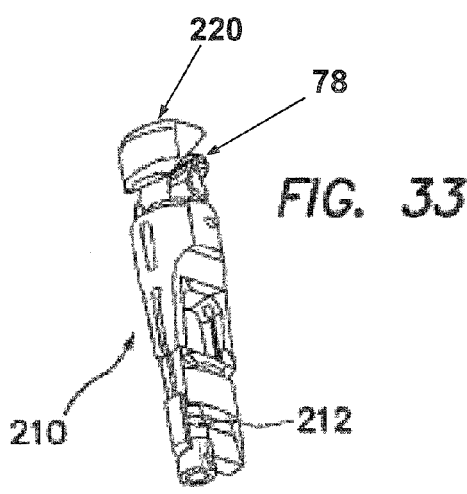
FIG. 33
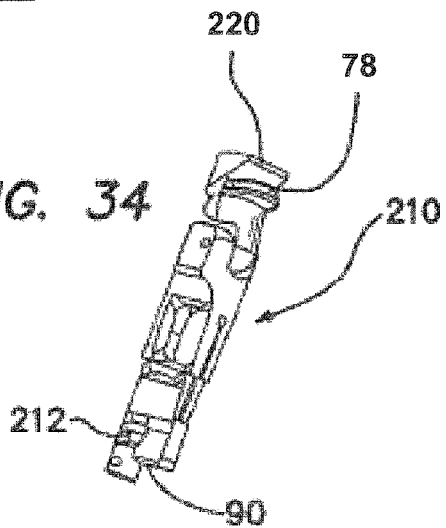
FIG. 34
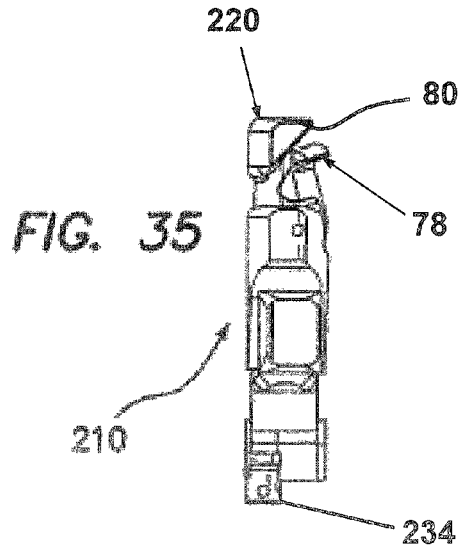
FIG. 35
FIG. 36

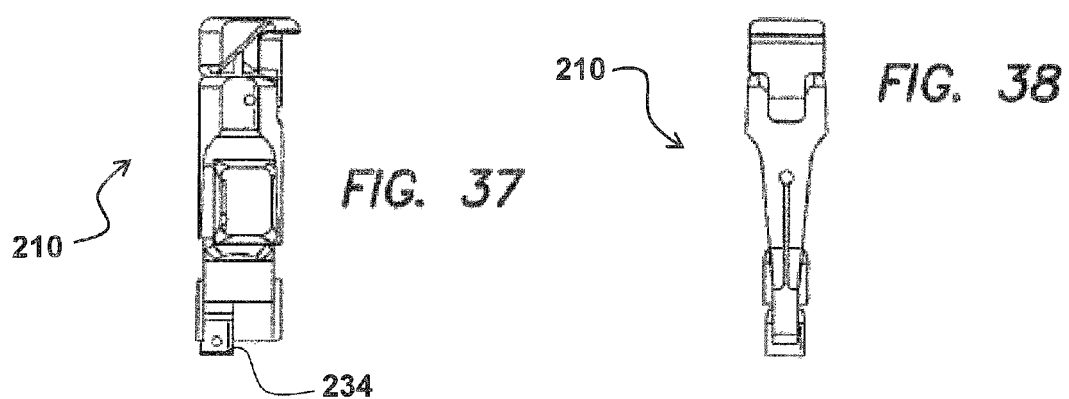
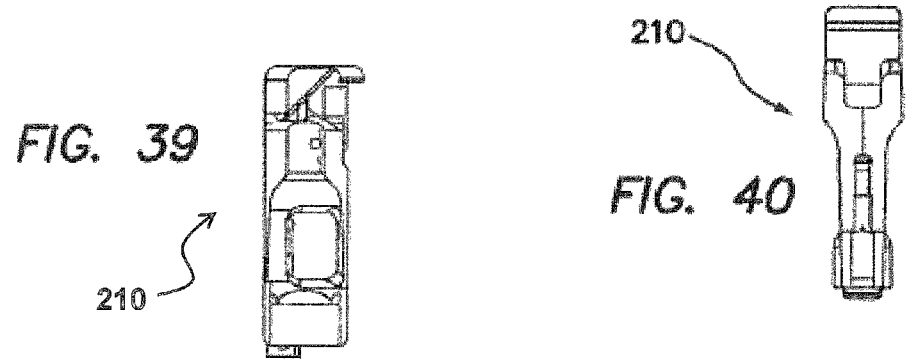
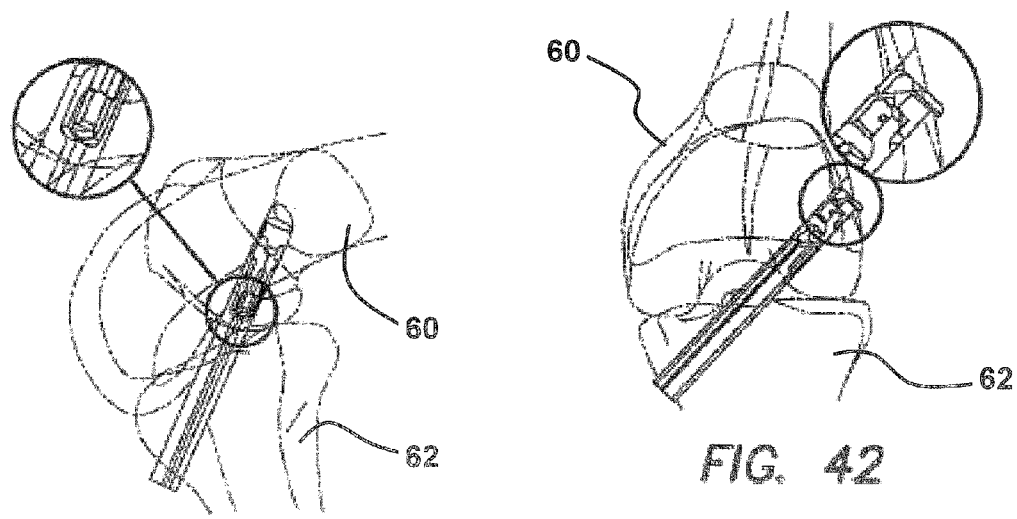

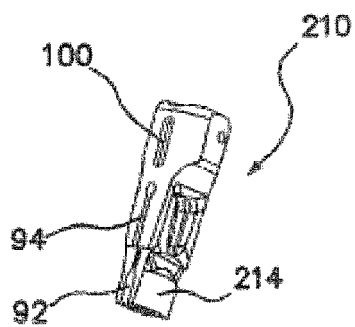
FIG. 43
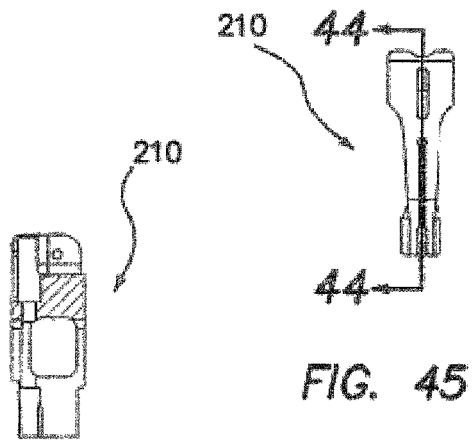
FIG. 44
FIG. 45
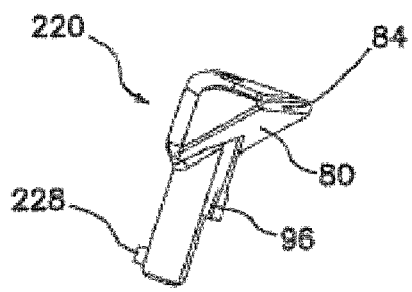
FIG. 46
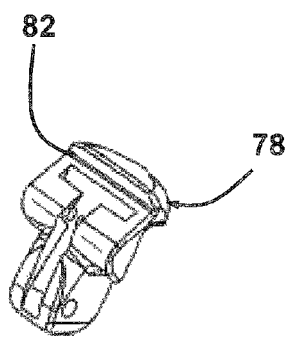
FIG. 47
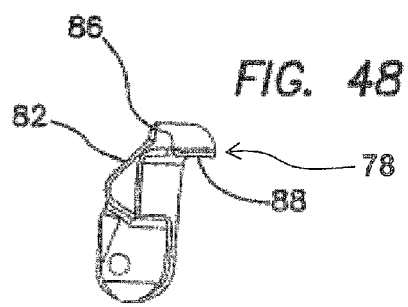
FIG. 48
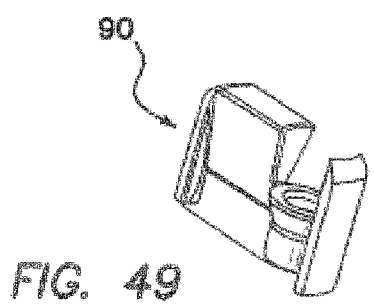
FIG. 49

METHODS AND SYSTEMS FOR MATERIAL FIXATION

This application is a divisional application under 35 U.S.C. 120 of commonly assigned U.S. patent application Ser. No. 11/923,526, entitled Methods and Systems for Material Fixation, filed Oct. 24,2007, now allowed, which in turn claims the benefit under 35 U.S.C. 119(e) of the filing date of Provisional U.S. Application Ser. No. 60/854,178, entitled Methods and Systems for Material Fixation, filed on Oct. 24, 2006. Each of the above referenced applications are which application is expressly incorporated herein by reference, in their entirety.

This application is also related to co-pending U.S. application Ser. No. 11/281,566 entitled Devices, Systems, and Methods for Material Fixation, filed on Nov. 18, 2005 and published as U.S. Patent Application Publication No. US 2006/0155287 on Jul. 13, 2006, and to co-pending U.S. application Ser. No. 11/725,981, entitled Devices, Systems, and Methods for Material Fixation, filed on Mar. 20, 2007. Both of these prior pending applications are commonly owned and herein expressly incorporated by reference.

BACKGROUND OF THE INVENTION

The present invention relates generally to devices, systems and methods for material fixation. More specifically, the present invention relates to a technique that can be used to firmly hold a soft tissue or graft against bone tissue within a bone tunnel.

One of the most common needs in orthopedic surgery is the fixation of tendon to bone. The fixation of diseased tendons into a modified position is called tenodesis and is commonly required in patients with injury to the long head of the biceps tendon in the shoulder. In addition, tendons which are torn from their insertion site into bone also frequently require repair. This includes distal biceps tendon tears, rotator cuff tears, and torn flexor tendons in the hand. Tendons are also frequently used in the reconstruction of unstable joints. Common examples include anterior cruciate ligament and collateral ligament reconstructions of the knee, medial and lateral elbow collateral ligament reconstructions, ankle collateral ligament reconstruction, finger and hand collateral ligament reconstructions and the like.

Traditional techniques that are used to fix tendon to bone suffer from a number of limitations as a result of the methodology used, including the use of a "keyhole" tenodesis, pull-out sutures, bone tunnels, and interference screw fixation. The "keyhole" tenodesis requires the creation of a bone tunnel in the shape of a keyhole, which allows a knotted tendon to be inserted into the upper portion, and subsequently wedged into the lower narrower portion of the tunnel where inherent traction on the tendon holds it in place. This technique is challenging as it is often difficult to sculpt the keyhole site and insert the tendon into the tunnel. In addition, if the tendon knot unravels in the postoperative period, the tendon will slide out of the keyhole, losing fixation.

Another traditional form of tendon fixation is the use of the "pull-out stitch." With this technique, sutures attached to the tendon end are passed through bone tunnels and tied over a post or button on the opposite side of the joint. This technique has lost favor in recent years due to a host of associated complications, which include wound problems, weak fixation strength, and potential injury to adjacent structures.

The most common method of fixation of tendon to bone is the use of bone tunnels with either suture fixation, or interference screw fixation. The creation of bone tunnels is relatively complicated, often requiring an extensive exposure to identify the margins of the tunnels. Drill holes placed at right angles are connected using small curettes. This tedious process is time-consuming and fraught with complications, which include poor tunnel placement and fracture of the overlying bone bridge. Graft isometry, which is easy to determine with single point fixation, is difficult to achieve because the tendon exits the bone from two points. After creation of tunnels, sutures must be passed through the tunnels to facilitate the passage of the tendon graft. Tunnels should be small enough to allow good tendon-bone contact, yet large enough to allow for graft passage without compromising the tendon. This portion of the procedure is often time-consuming and frustrating to a surgeon. Finally, the procedure can be compromised if the bone bridge above the tunnel breaks, resulting in loss of fixation. The technique restricts fixation to the strength of the sutures, and does not provide any direct tendon to bone compression.

More recent advances in the field of tendon fixation involve the use of an internally deployed toggle button, for example, the EndoButton ®, and the use of interference screws to provide fixation. The EndoButton, by Smith & Nephew, allows the fixation of tendon into a bone tunnel by creating an internally deployed post against a bony wall. While this technique eliminates the need for secondary incisions to place the post, the fixation strength is limited to suture strength alone. This technique does not provide direct tendon to bone compression; as such this technique may slow healing and lead to graft tunnel widening due to the "bungee effect" and "windshield wiper effect". As a result, this technique has limited clinical applications and is used primarily for salvage when bone tunnels break or backup fixation is important.

The use of the interference screw is the most notable advance in the fixation of tendon to bone. The screw is inserted adjacent to a tendon in a bone tunnel, providing axial compression between the screw threads and the bony wall. Advantages include acceptable pull-out strength and relative ease of use. Aperture fixation, the ability to fix the tendon to bone at its entrance site, is a valuable adjunct to this technique as it minimizes graft motion and subsequent tunnel widening. Some disadvantages related to soft tissue interference screws are that they can be difficult to use, and can also cut or compromise the tendon during implantation.

The newest generation interference screw allows the ability to provide tendon to bone fixation with limited exposure. For example, the Bio-Tenodesis Screw™ (Arthrex, Inc.) allows the tensioning and insertion of tendon into bone, followed by insertion of an adjacent soft tissue interference screw. While this screw system provides advantages in the insertion of tendon into bone in cases when a pull through stitch is not available, it is still limited by the potential for tendon rotation or disruption as the screw compresses the tendon. The surgical technique is also complicated, typically requiring two or more hands for insertion, making it difficult to use the system without assistance during arthroscopic or open procedures. Finally, the use of the screw requires preparation of the tendon end, which can be difficult, time consuming, and can also require conversion of an arthroscopic procedure to open.

Referring particularly to the field of repairing an anterior cruciate ligament (ACL) injury, current repair techniques utilizing soft tissue for the replacement graft are either difficult to perform or they result in less than favorable outcomes due to their relatively low tendon-to-bone fixation. Existing ACL reconstruction techniques that have acceptable outcomes (high tendon-to-bone fixation strength) require extra operating room time and surgeon effort due to the requirements of multiple drill holes, external guides and fixtures for the drill holes, and multiple assistants. Another difficulty with current techniques is that they do not well replicate the native ACL in its anatomy or physiology.

Two important factors in replicating the native ACL are aperture compression (compressing the tendon against the bone at the opening of the drill hole into the joint) and tendon length. Compression of the tendons at the aperture of the femoral tunnel will improve the healing process by increasing the intimate contact between the tendon and the bone. Studies show that the lack of intimate contact between the tendon and bone can result in less well organized fibrous tissue, resulting in lower pull-out strengths. The stiffness of the repair is also important to replicate the native ACL. Graft stiffness is decreased by the length of tendon between the fixation points.

Currently, two different sources are utilized for the tissue that replaces the injured native ACL. When the new tissue comes from the patient's own body, the new graft is referred to as an autograft, and when cadaveric tissue is used, the new graft is referred to as an allograft. The most common autograft ACL reconstruction performed currently is the bone-patellar tendon-bone (BTB) graft. The BTB graft fixed with an interference screw is used more often because it more accurately replicates the native ACL, due to its aperture compression at the femoral tunnel aperture. However, BTB reconstructions result in an increased rate of anterior knee pain post-surgically for periods of up to 3 years after the reconstruction. Additionally, the harvest procedure for the BTB autograft is invasive and can be difficult to perform. Alternatively, the hamstring tendon autograft ACL reconstruction technique does not result in any significant post-surgical pain, and the harvest procedure is minimally invasive compared to the BTB graft harvest. The reason that the hamstring tendon autograft procedure is not used more frequently in ACL reconstructions is that the fixation of the hamstring tendons to the femur and tibia are not as strong as the fixation of the BTB autografts.

Many prior art systems have addressed some of the problems associated with ACL reconstruction using hamstring tendons, but there is not one system that addresses them all. For example, the EndoButton system (Smith & Nephew) is easy to use and does not need additional drill holes. However, it does require additional accessories and additional people to perform the procedure and does not replicate the native ACL due to a lack of tendon-to-bone compression at the aperture, as well as additional length of tendon between fixation points. The EndoButton system is an example of a cortical hamstring fixation device that yields a longer graft construct, resulting in a graft that is less stiff than the native ACL. Peer reviewed journal data show that existing soft tissue fixation systems with long graft lengths between fixation points have as much as a 56% reduction in graft stiffness when compared to the native ACL.

The RigidFix® product by Mitek is a cross pin device that requires multiple drill holes, additional instruments, and assistance from other people in the operating room to complete the repair. Also, there is only passive compression of tendon to bone, not direct, active compression.

The Stratis® ST product by Scandius attempts to more accurately replicate the native ACL by adding material to take up space in the femoral tunnel resulting in more intimate contact between the tendon and the bone. However, to insert the device into the femoral tunnel, the cross-sectional area must be less than the cross-sectional area of the hole. Thus, there is no real compression of tendon to bone. The Stratis ST product also requires additional drill holes, accessories, and people to properly perform the procedure.

The EZLOC™ product by Arthrotek provides high strength and attempts to more accurately replicate the native ACL in the same fashion as the Stratis ST product, by taking up the space in the femoral tunnel. This does create more intimate contact between the tendon and bone, but does not offer real compression at the aperture.

Interference screws such as the RCI™ Screw, available from Smith & Nephew, are easy to use and provide compression of tendon to bone at the femoral tunnel aperture. However, the pull-out strength and stiffness of the repair are significantly lower than the preceding systems.

Thus, although there are many conventional techniques used for the fixation of tendon to bone, each having some advantages, the disadvantages of each such technique presents a need in the art for a simple and universal technique to fixate tendon to bone such that the device is easy to use, the process is simple to follow, and the result is a firm and secure tendon to bone fixation with minimal negative effect on the tendon. Further, such device should be easy to manufacture, universally applied to different tendon to bone sites, and require minimal effort to understand and use in practice.

SUMMARY OF THE INVENTION

The present invention is a device that is easy to use, provides high fixation of tendon-bone and active tendon-bone compression, requires no additional accessories, uses only one drill hole, and can be implanted by one practitioner. The invention utilizes cancelous bone for fixation, and replicates the native ACL by compressing the tendons against the bone at the aperture of the femoral tunnel, effectively shortening the length of the graft as compared to cortical hamstring fixation devices. An important advantage of the invention is the improvement of the tendon-bone fixation of hamstring autografts as well as other soft-tissue ACL reconstruction techniques. Extra graft length is eliminated by compression of the tendon against the bone at the aperture of the femoral tunnel, which more closely replicates the native ACL and increases graft stiffness. The inventive device provides high fixation of tendon to bone and active tendon-bone compression. Graft strength has been found to be greater than 1,000 N (Newtons), which is desirable for ACL reconstruction systems.

More particularly, there is provided in one aspect of the invention a material fixation system, which comprises an implant which is placeable in a tunnel disposed in a portion of bone, wherein the tunnel is defined by walls comprised of bone. A first member is deployable outwardly to engage the tunnel walls for anchoring the implant in place in the tunnel, and a second member is deployable outwardly to engage tissue material to be fixed within the tunnel. The second member also functions to move the tissue material outwardly into contact with the tunnel walls. A third member forming a part of the implant is movable to deploy the first member outwardly. A fourth member is provided actuating the third member to move in order to deploy the first member.

Preferably, the fourth member comprises a portion which functions to deploy the second member outwardly. The implant comprises a body having a distal end and a proximal end, and the first member is disposed on the body. The first member comprises an arm which is pivotally attached to the body. The third member comprises a wedge which is movable generally axially to deploy the arm.

In one presently preferred embodiment, the fourth member comprises a deployment screw having a distal end and a proximal end, wherein the deployment screw is adapted to extend axially through the body. The distal end of the deployment screw has a threaded portion which is engageable with a complementary threaded portion on the wedge, wherein rotation of the deployment screw causes relative movement of the deployment screw and the wedge. The wedge moves proximally to deploy the arm.

The aforementioned second member comprises a compression pad. In the preferred embodiment, the fourth member portion comprises a head of the deployment screw, disposed on the proximal end thereof.

In another aspect of the invention, there is provided an anchor for securing soft tissue into a portion of bone, which comprises a body portion having a distal end and a proximal end. At least one outwardly deployable anchoring member is disposed on the body. A wedge member is movable for deploying the at least one outwardly deployable anchoring member. The anchor further comprises a generally axially movable deploying member for moving the wedge member. The deploying member engages the wedge member to move the wedge member, and is disposed proximally of the wedge member.

Preferably, the aforementioned wedge member is disposed distally of the outwardly deployable anchoring member, and moves proximally in order to deploy the outwardly deployable anchoring member outwardly. The anchor further comprises an outwardly deployable compression member for engaging a portion of soft tissue and pushing the soft tissue outwardly into contact with adjacent bone. The outwardly deployable compression member is proximal to the outwardly deployable anchoring member. A portion of the generally axially movable deploying member is adapted to deploy the compression member outwardly. Again, referencing currently preferred embodiments, the at least one outwardly deployable anchoring member comprises an arm pivotally attached to the body, and the generally axially deploying member comprises a threaded deployment screw.

In yet another aspect of the invention, there is provided an implant system for use in making an orthopedic repair of a joint, which comprises a first implant adapted for receiving a tissue graft thereon and then being disposed in a first bone tunnel location, wherein ends of the tissue graft extend through a bone tunnel and out of a proximal end of the tunnel. The first implant comprises a body portion having a distal end and a proximal end, and a first member disposed on the body portion which is deployable outwardly to engage adjacent bone for anchoring the implant in place in the tunnel. The first implant further comprises a second member disposed on the body portion which is deployable outwardly to engage tissue material to be fixed within the tunnel, and to move the tissue material outwardly into contact with the tunnel walls. The implant system further comprises a second implant adapted for disposition in a second bone tunnel location, proximal to the first bone tunnel location. The second implant is adapted to secure the ends of the tissue graft which extend from the first implant against adjacent bone. The first implant further comprises a third member which is movable to deploy the first member outwardly. A fourth member is provided for actuating the third member to move in order to deploy the first member.

In still another aspect of the invention, there is disclosed a method of making an orthopedic repair by fixing a soft tissue graft to bone, which comprises steps of placing a soft tissue graft on an implant, and disposing the implant within a bone tunnel at a desired location, such that a plurality of ends of the soft tissue graft extend from the implant in a proximal direction through the bone tunnel. Additional steps include deploying a first member on a body of the implant outwardly so that portions of the first member engage adjacent bone to secure the implant in place at the desired location, and deploying a second member on the body of the implant outwardly, so that portions of the second member engage portions of the plurality of ends of the soft tissue graft and push the soft tissue graft ends into contact with adjacent bone.

The invention, together with additional features and advantages thereof, may best be understood by reference to the following description taken in conjunction with the accompanying illustrative drawing.

BRIEF DESCRIPTION OF THE DRAWINGS

FIG. 1 is an isometric view of an embodiment of a device constructed in accordance with the principles of the present invention;

FIG. 2A is a top view of the device of FIG. 1 in an undeployed configuration;

FIG. 2B is a side view of the device of FIG. 2A;

FIG. 3A is a top view of the device of FIG. 1, wherein the deployment screw is starting to deploy the compression pads;

FIG. 3B is a side view of the device of FIG. 3A;

FIG. 17 is a table summarizing the performance of an implant constructed in accordance with the principles of the present invention, as shown in FIGS. 1-7;

FIG. 32 is a data table;

FIG. 33 is an isometric view of another embodiment of the invention, comprising an undeployed cortical fixation implant;

FIG. 34 is an isometric view of the cortical fixation implant of FIG. 33, from a different orientation;

FIGS. 35 and 36 are top and side views, respectively, of the cortical implant of FIGS. 33 and 34;

FIGS. 37 and 38 are top and side views, respectively, of the cortical implant of FIGS. 33 and 34, wherein the implant is beginning to be deployed;

FIGS. 39 and 40 are top and side views, respectively, of the cortical implant of FIGS. 37 and 38, wherein the implant is in a deployed state;

FIGS. 41 and 42 show a deployment sequence for the cortical fixation implant;

FIG. 43 is an isometric view of the body of the implant of FIG. 33, showing integrated compression pads;

FIG. 44 is a cross-sectional view of the body of FIG. 43, taken along the lines 44-44 of FIG. 45;

FIG. 45 is a side view of the implant of FIG. 43;

FIG. 46 is a perspective view of the wedge of the invention;

FIGS. 47 and 48 are views of the arm of the invention;

FIG. 49 is a perspective view of the compression wedge of the invention;

FIGS. 51-52 are isometric views of an additional embodiment of a cortical implant of the invention, wherein FIG. 51 shows the device in its undeployed configuration and FIG. 52 shows the device in its deployed configuration;

FIGS. 53-54 are isometric views of still another embodiment of a cortical implant of the invention, wherein FIG. 53 shows the device in its undeployed configuration and FIG. 54 shows the device in its deployed configuration.

DETAILED DESCRIPTION OF THE INVENTION

Figure 4A:
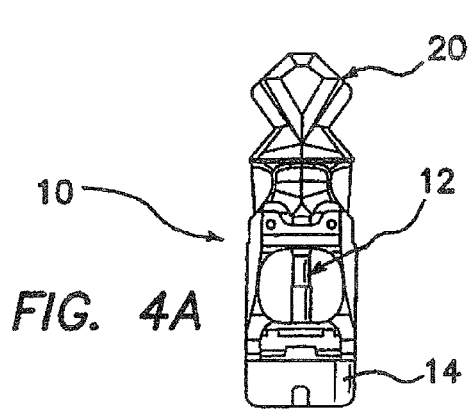
FIG. 4A is a top view of the device of FIG. 1, wherein the compression pads have been fully deployed.

Referring now more particularly to the drawings, procedures and anchoring devices for repairing soft tissue are illustrated. In FIG. 1, one embodiment of an implant 10, constructed in accordance with the principles of the present invention, is shown. The implant 10 comprises a deployment screw 12, which protrudes through a pair of compression pads 14 and 16. The implant 10 comprises a body 18, through which the deployment screw 12 also protrudes. The deployment screw 12, at its distal end, is threaded into a wedge 20.

The left compression pad 14 slides into the right compression pad 16, and they attach to one another. Two pins 22 attach a pair of arms 24 to the body 18. There is a track 26 on each side of the wedge 20, best seen in FIG. 14A. Each wedge track 26 attaches to a track post 28 (FIG. 13B) on a corresponding one of the arms 24. The wedge tracks 26 function to prevent the wedge from rotating during deployment of the implant.

Figure 4B:
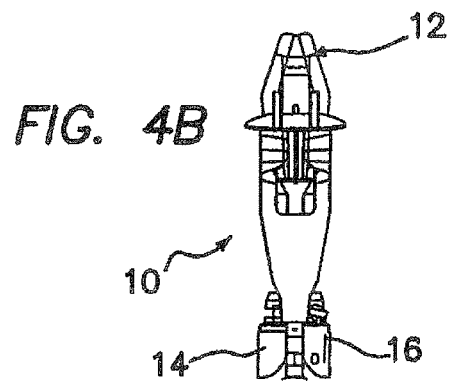
FIG. 4B is a side view of the device of FIG. 4A.

The compression pads 14, 16 slide into a pair of body tracks 30 (FIG. 12) in the body 18, which allow the pads 14, 16 to expand when the deployment screw 12 is rotated clockwise, as shown in FIGS. 2-4. The body tracks 30 also prevent the pads 14, 16 from rotating.

Figure 10:
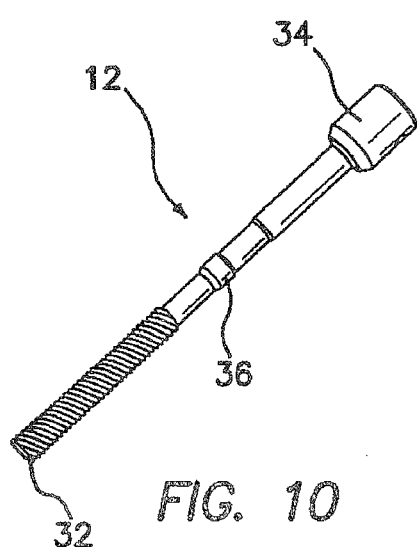
FIG. 10 is a perspective view, in isolation, of a deployment screw for use in the embodiment of FIGS. 1-7.

In FIG. 10, the deployment screw 12 is shown in detail. This screw 12 comprises a quad lead section 32, with four separate thread starts. This means that, for every single turn on the screw, the linear distance it travels is four times what a single lead screw would be. This feature enables the user to turn the screw fewer times than would be required with a single start thread, approximating the same number of turns that the user would need during the implantation of an interference screw such as the above described Smith & Nephew RCI screw. Often, during implantation, an interference screw requires a notch to be placed at the edge of the femoral tunnel aperture to allow the screw to start engaging into the bone. Advantageously, the need for this step is eliminated when deploying the implant of the present invention, resulting in a substantially easier implementation procedure.

Accordingly, the present invention is easy to deploy as an interference screw, and requires fewer steps than in prior art approaches. The deployment screw 12 also provides a rigid backbone to support the implant. A screw head or compression pad deployer 34 deploys the compression pads 14, 16 as the screw 12 moves axially into the implant. Another feature of the screw 12 is a load transfer disk 36 that transfers some of the axial load from a junction between the screw head 34 and the body 18 to a junction between the load transfer disk 36 and the body 18. This load transferring feature allows for thinner side walls or struts 38 on the body 18 due to a decreased load on struts 38 (FIG. 12), which, in turn, allows a larger tendon to fit between the deployment screw 12 and the body 18.

Figure 11A:
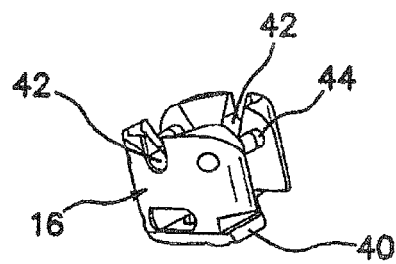
FIG. 11A is a perspective view of a compression pad for use in the embodiment of FIGS. 1-7.
Figure 11B:
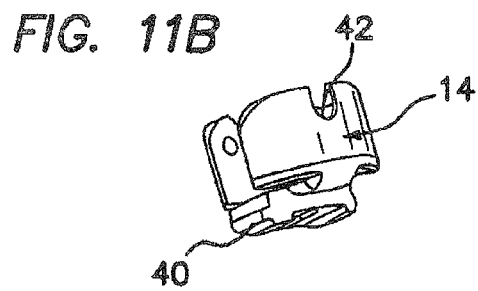
FIG. 11B is a perspective view of a second compression pad.

With reference now particularly to FIGS. 11A and 11B, the compression pads 14 and 16 are shown in greater detail. The left and right compression pads 14, 16, respectively, compress the tendons against the femoral tunnel wall to promote tendon-to-bone healing at the aperture of the tunnel. Unlike current approaches for more intimate tendon-to-bone contact that only reduce the space between the tendon and the tunnel wall, the present invention actively compresses the tendons against the bone tunnel. Compression pad tracks 40 engage the body tracks 30 and interlock them to the body 18. This joint also provides torsional resistance while moving the implant into place, and during initial deployment until the arms 24 start to engage with the bone. There are engagement slots 42 in each compression pad 14, 16, as shown, that engage with a deployment device that keep the implant 10 from rotating until the arms 24 engage the bone. The two compression pads 14, 16 snap together using compression pad snaps 44 to prevent premature deployment of the pads.

Figure 12:
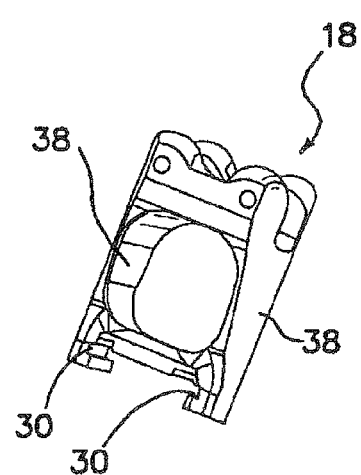
FIG. 12 is a perspective view of the body of the implant of FIGS. 1-7.

Now referring to FIG. 12, the body 18 functions to trap the tendons on either side of the deployment screw 12. The compression pads 14, 16 engage the body tracks 30 and provide torsional strength to the body while inserting the implant into the femoral tunnel, thus allowing the compression pads 14, 16 to expand parallel to one another. The struts 38 also provide structural support for the deployment screw 12, wedge 20, and arms 24 to deploy against.

Figure 13A:
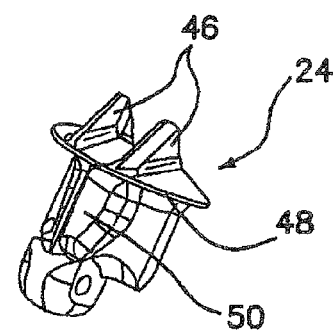
FIGS. 13A and 13B are perspective views of arms for use in the embodiment of FIGS. 1-7.
Figure 13B:
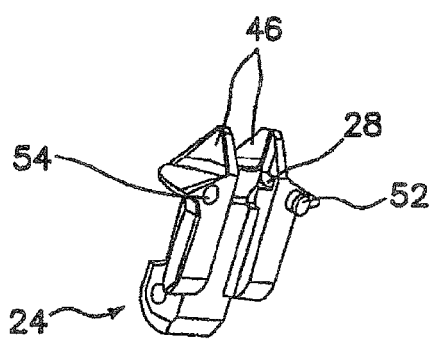

The arms 24 have a few key design features, as best shown in FIGS. 13A and 13B. Fins 46 on the top of each arm provide torsional strength for the wedge-to-arm junction. The fins 46 also allow easier insertion into the femoral tunnel when inserting into a femoral tunnel that is drilled off-axis from the tibial tunnel. The portion of the arm 24 that engages with the bone has a tapered edge 48 which allows for ease of bone displacement during deployment. A support rib 50 disposed along the length of the arm 24 is also tapered for ease of bone displacement, and provides structural support during axial loading. Torsion pins 52 engage with a torsion hole 54 to provide additional torsional strength while the implant is being implanted into the femoral tunnel.

Figure 14A:
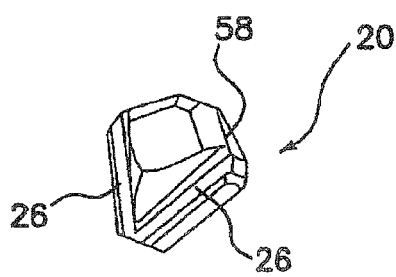
FIGS. 14A and 14B are perspective views of the wedge for use in the embodiment of FIGS. 1-7.
Figure 14B:
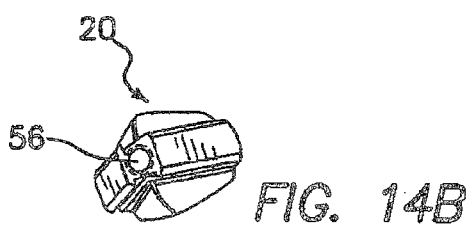

FIGS. 14A and 14B show, in greater detail, particular constructional features of the wedge 20. The wedge 20 is threaded with a female quad lead thread 56 that matches the male quad lead thread 32 of the deployment screw 12. The track posts 28 engage with the wedge tracks 26 to provide torsional strength through deployment. A tapered nose 58 on the wedge 20 allows easier off-axis insertion into the femoral tunnel.

Referring now to FIGS. 2-9, a preferred method of using the disclosed inventive implant will now be discussed. In FIGS. 2A and 2B, the implant 10 of FIG. 1 is shown in its undeployed orientation. A preferred procedure for deploying the implant is generally similar in many respects to the procedure disclosed in U.S. Patent Application Publication No. 2006/0155287, herein already expressly incorporated by reference.

Thus, to accomplish tendon fixation using the exemplary methods and devices described herein, standard surgical preparation of the site and/or arthroscopic portals for access to the procedural region are performed. The joint is dilated with arthroscopic fluid if the procedure is to be performed arthroscopically. With open procedures, the device may easily be manipulated and deployed with a single hand. For arthroscopic procedures, the deployment device is introduced through a standard 5, 6, or 8 mm cannula placed into the joint. A range of preferred cannula sizes would be 2-11 mm.

The procedures described herein are specifically adapted to repair of the ACL in a patient's knee. However, it should be kept in mind that the implants described herein may be used in numerous other soft tissue repair applications, using surgical procedures which are adapted to those applications.

Figure 8:
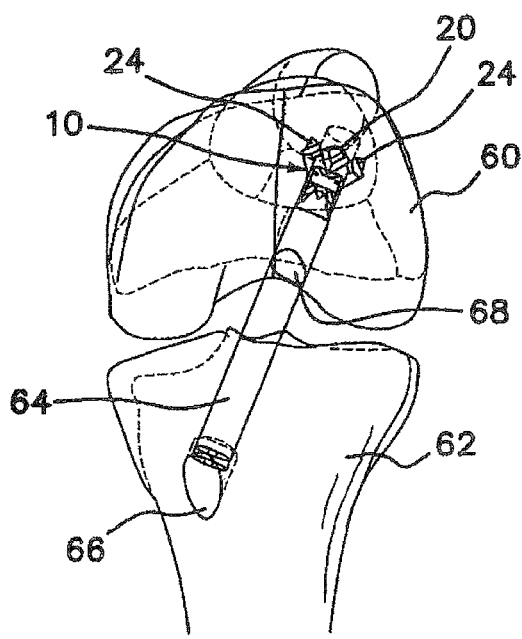
FIG. 8 is a view illustrating the implant of FIG. 1, as it is deployed in the femoral tunnel of a patient.
Figure 9A:
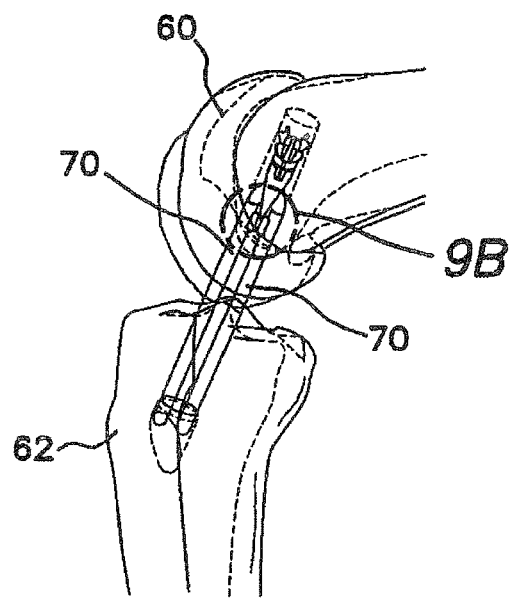
FIG. 9A is a view illustrating tendon compression as effected by the embodiment of FIGS. 1-7.

FIGS. 8 and 9A illustrate, from two different orientations, a hamstring ACL reconstruction, wherein the implant 10 is utilized to secure the ACL graft proximal to the femur 60 and distal to the tibia 62 of a patient. To deploy the implant 10, a bone tunnel 64 is drilled completely through the tibia 62 and partially through the femur 60. An actuator (not shown) is employed to insert the implant 10 distally through a tibial inlet aperture 66 and through the tibial tunnel 64, so that the implant 10 is finally disposed in a portion of the tunnel 64 which is within the femur 60, distal to a femoral aperture 68, as shown in FIGS. 8 and 9A.

Now with respect to FIGS. 3 and 3A, once the implant 10 is in place within the femoral tunnel 64, as shown in FIG. 8, the deployment screw 12 is actuated (rotated) in order to advance the screw 12 axially distally into the implant body 18, and thus begin to deploy or expand the compression pads 14 and 16 outwardly. FIGS. 4 and 4A depict the next step, wherein advancement of the deployment screw 12 has caused the compression pads 14, 16 to fully deploy. As noted above, the screw head or compression pad deployer 34 acts to deploy the compression pads 14, 16 as it moves distally into the implant 10, as shown.

Figure 5:
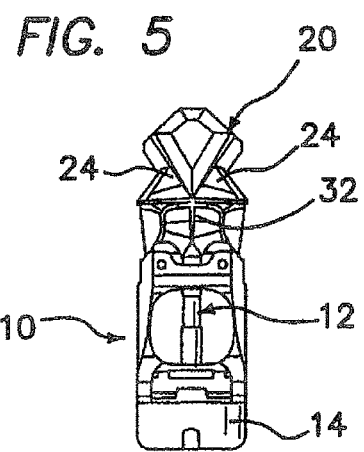
FIG. 5 is a top view of the device of FIG. 1, wherein the wedge is starting to deploy the arms.
Figure 6:
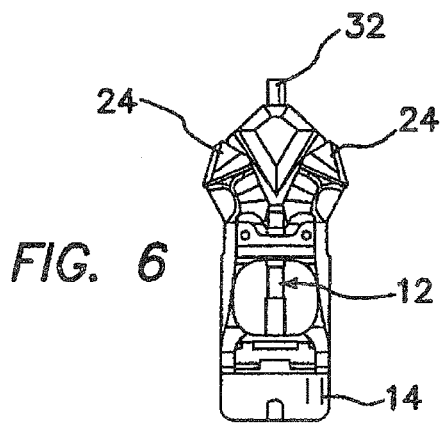
FIG. 6 is a top view of the device of FIG. 1, wherein the wedge is halfway engaged.

As the deployment screw 12 continues to move distally through the implant 10, the distal end of the screw 12, comprising the male quad lead section 32 (FIG. 10), engages the female quad lead thread 56 of the wedge 20 (FIG. 14B). Continued axial distal movement of the screw 12 causes the threaded sections 32 and 56 to cooperate to move the wedge 20 axially in a proximal direction, as shown in FIG. 5. This proximal movement of the wedge 20 causes the arms 24 to begin to deploy outwardly. In FIG. 6, the wedge 20 is shown in a position where it is about halfway engaged within the separating arms 24.

Figure 7A:
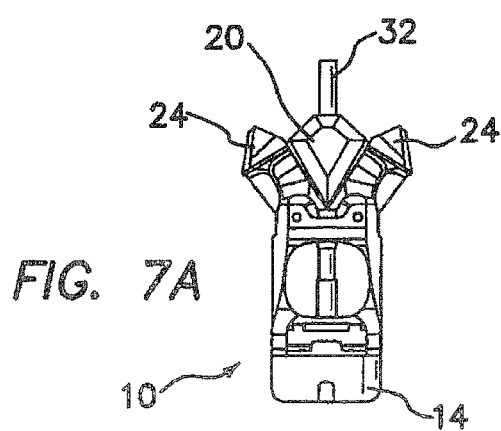
FIG. 7A is a top view of the device of FIG. 1, wherein the implant has been fully deployed.
Figure 7B:
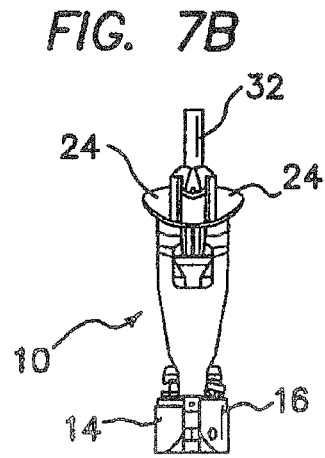
FIG. 7B is a side view of the device of FIG. 7A.

In FIGS. 7A and 7B, the wedge 20 is fully proximally engaged with the body 12 of the implant 10, such that the arms 24 are, consequently, fully deployed. In FIG. 8, the implant 10 is shown in this fully deployed condition.

Figure 9B:
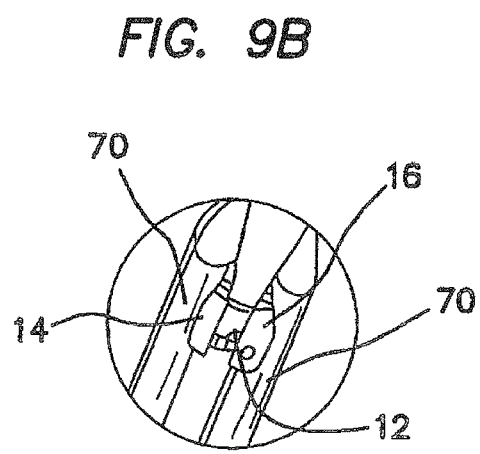
FIG. 9B is a detail view of a portion of FIG. 9A denoted by a circle labeled as "9B"

FIGS. 9A and 9B illustrate tendon compression as effected by the deployed implant 10. In these figures, tendons 70 are compressed by deployed compression pads 14, 16 against the femoral tunnel wall in order to promote tendon-to-bone healing at the aperture of the tunnel. Advantageously, the inventive approach actively compresses the tendons against the bone tunnel.

Figure 15A:
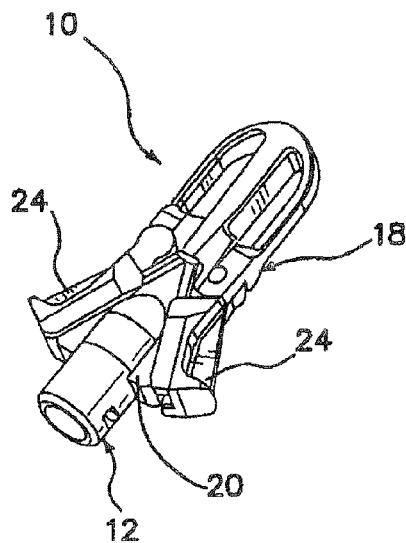
FIGS. 15A and 15B are perspective views of modified embodiments of the implant of FIGS. 1-7 with arms flipped to engage with the cortical surface during a soft tissue repair procedure.
Figure 15B:
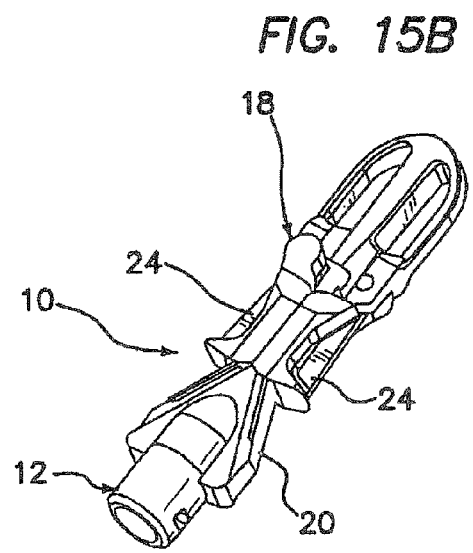

Alternative implant designs are shown in FIGS. 15 and 16. In particular, FIGS. 15A and 15B illustrate an alternative embodiment (with like elements being labeled with like reference numerals to those used in connection with the embodiment of FIG. 1) wherein the arms 24 are flipped to the other side of the body 18. The modified arms 24 are designed to permit the tendons (not shown) to pass by them and engage with the cortical bone. The arm-to-body joint is a pin-less design with a track way in the body that secures the arm 24 in place.

Figure 16A:
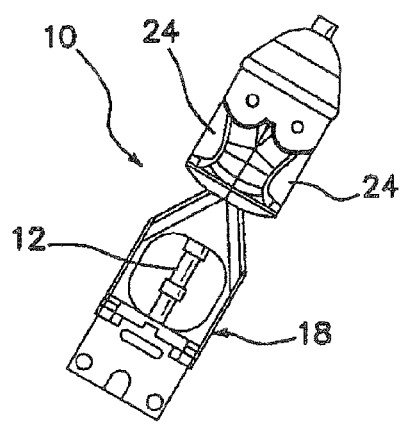
FIGS. 16A and 16B are perspective views of yet another embodiment of the implant of the invention, wherein the body is used as the wedge.
Figure 16B:
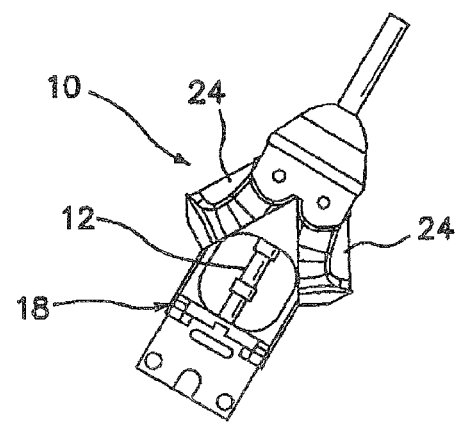
Figure 18:
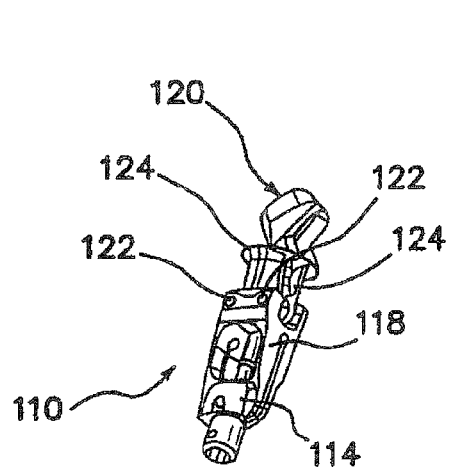
FIG. 18 is an isometric view of a further modified embodiment of the invention.
Figure 19:
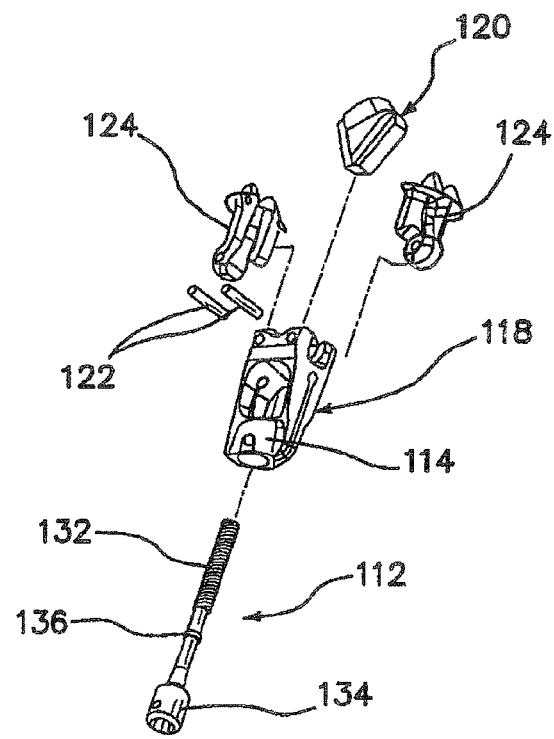
FIG. 19 is an exploded view of the embodiment of FIG. 18.
Figure 20:
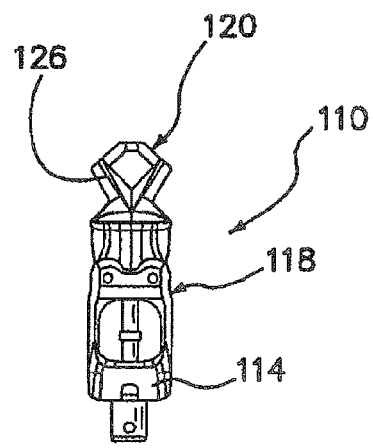
FIG. 20 is a plan view of the embodiment of FIG. 18, in an undeployed configuration.
Figure 21:
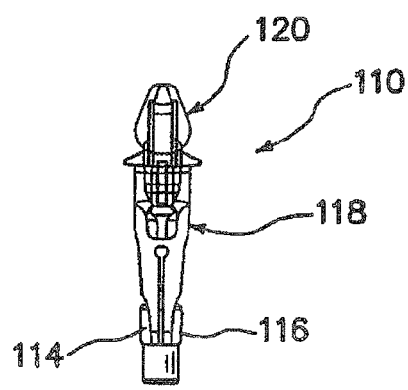
FIG. 21 is a side view of the embodiment of FIG. 20.
Figure 23:
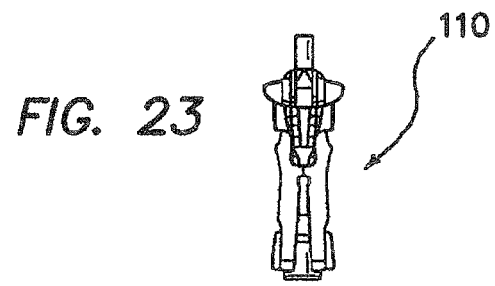
FIG. 23 is a side view of the embodiment of FIG. 22.
Figure 22:
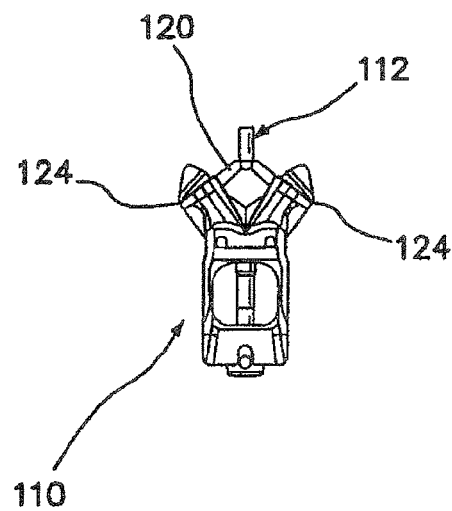
FIG. 22 is a plan view of the embodiment of FIG. 20, wherein the deployment screw is starting to deploy the compression pads.

FIGS. 16A and 16B illustrate yet another modified embodiment wherein, once again, like elements are labeled with like reference numerals as those used in connection with the earlier embodiments. In this embodiment, the implant 10 uses the body 18 as a wedge.

Testing has been done by the inventors to verify the functionality of the disclosed invention of FIGS. 1-7. As shown in FIG. 17, the inventors found that pull-out forces for the implant 10 were significantly higher than those of a predicate device, the RCI interference screw available from Smith & Nephew.

In FIGS. 18-21 there is shown another implant embodiment 110, wherein like elements are identified with like reference numerals as for the embodiment of FIGS. 1-14, preceded by the numeral 1. As shown, the deployment screw 112 protrudes through the compression pads 114 and 116, which are each integrated into the body 118. The deployment screw 112 is threaded at its distal end into the wedge 120. Two pins 122 attach a pair of arms 124 to the body 118, as shown.

Figure 24:
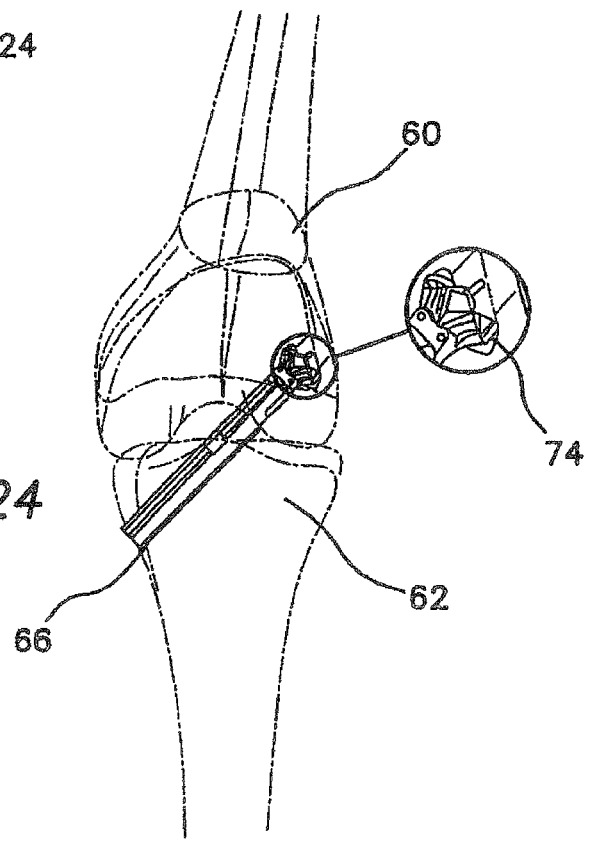
FIG. 24 is a view illustrating the implant of FIGS. 18-23 deployed in a femoral tunnel.
Figure 27:
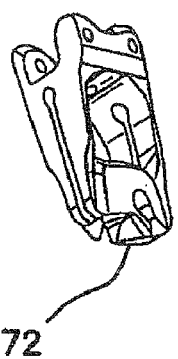
FIG. 27 is a view showing the body of the implant.

As noted above, in this embodiment the compression pads 114, 116 are 25 integrated into the body 118. This feature permits the use of a shorter implant than is the case for the implant of FIG. 1. A track 126 in the wedge 120 attaches to track posts 128 on the arms 124 (FIG. 29), which keep the wedge 120 from rotating during deployment. The compression pads expand as the implant is deployed. In particular, the screw 112 expands the pads 114, 116 outwardly by sliding on a compression taper 72 (FIG. 27), as shown in FIGS. 20-23. Moreover, as the deployment screw 112 rotates, the wedge 120 expands the arms 124 as also shown in FIGS. 20-23. Once the screw 112 is fully seated, the expanded arms 124 fully engage with adjacent cancellous bone 74, thus locking the anchor in place, as shown in FIG. 24.

Figure 26:
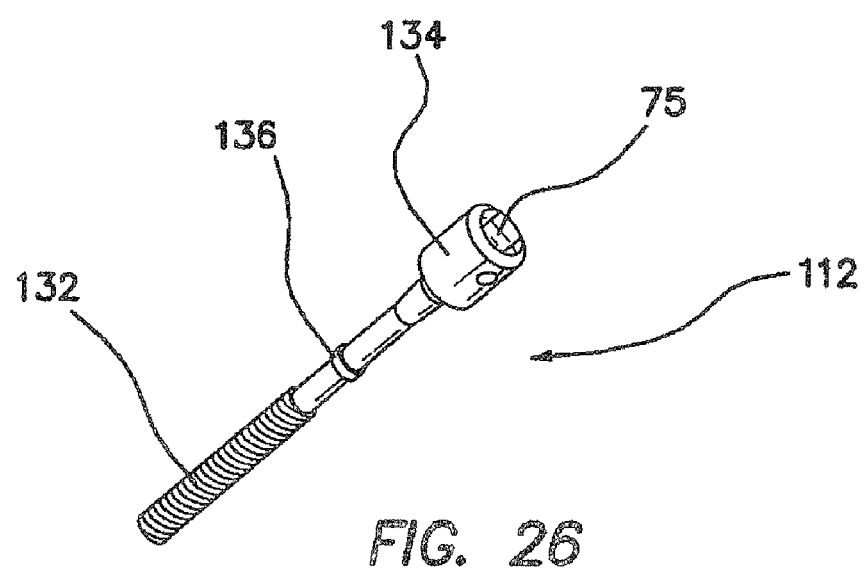
FIG. 26 is a perspective view of the deployment screw.

The deployment screw 112 (FIG. 26) has a male quad lead section 132 with four separate thread starts, as in the prior disclosed embodiment. This means that for every one rotation of the screw, the linear distance it travels is four times that which a single lead screw would travel. This enables the user to turn the screw fewer times than would be required with a single start thread, approximating the same number of turns that the user would need during the implantation of an interference screw such as the RCI screw available from Smith & Newphew. Oftentimes, during implantation, an interference screw such as the RCI screw requires a notch to be placed at the edge of the femoral tunnel aperture to permit the screw to start engaging the bone. However, the present invention avoids the need for such a step, resulting in an easier implantation procedure. The invention is easy to deploy as an interference screw, and requires fewer steps. The deployment screw 112 also provides a rigid backbone to support the implant. A reverse threaded hex 75 is preferably provided to drive the screw.

The screw head or compression pad deployer 134 deploys the compression pads 114, 116 as the screw 112 advances axially into the implant. Another feature of the screw is the provision of a load transfer disk 136 that transfers some of the axial load from the screw head 134 to body junction to the disk to body junction. This allows for thinner side walls or struts 138 on the body 118 due to the decreased load on the struts, which in turn allows a larger tendon to fit between the deployment screw 112 and the body 118.

Figure 25:
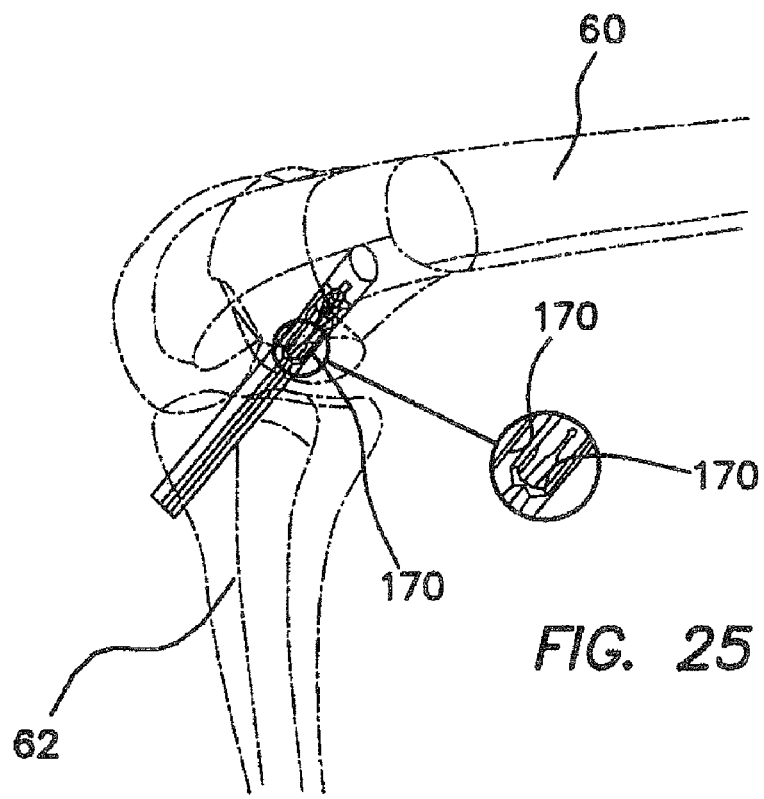
FIG. 25 is a detailed view similar to FIG. 24, showing tendon compression performed by the deployed inventive device.

As shown in FIG. 25, the compression pads 114, 116 compress the tendons 170 against the femoral tunnel wall to promote tendon-to-bone healing at the aperture of the tunnel. Unlike prior art approaches for more intimate tendon-to-bone contact that only reduce the space between the tendon and the tunnel wall, the present invention actively compresses the tendons against the bone tunnel. The compression pads 114, 116 in this embodiment are integral with the body 118.

Figure 28:
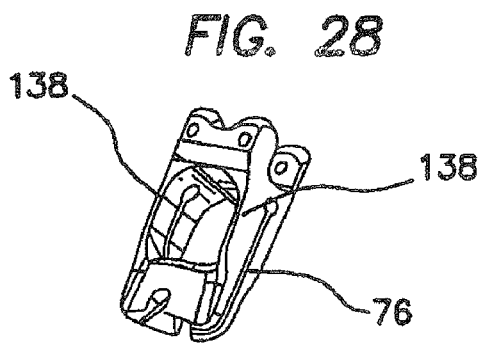
FIG. 28 is a view similar to FIG. 27, but showing the implant from a different orientation.

The body 118 functions to trap the tendons 170 on either side of the deployment screw 112. The struts 138 are split, as shown at reference numeral 76 (FIG. 28), to allow the integrated compression pads 114, 116 to expand and compress the tendon against the bone tunnel. They also provide structural support for the deployment screw 112, wedge 120, and arms 124 to deploy against.

Figure 29:
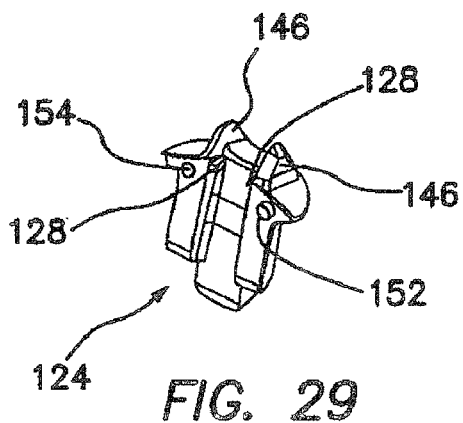
FIG. 29 is an isometric view of an arm in accordance with the invention.
Figure 30:
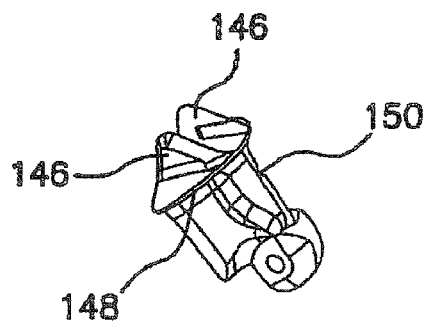
FIG. 30 is an isometric view from a different orientation than FIG. 29, showing the arm.
Figure 31:
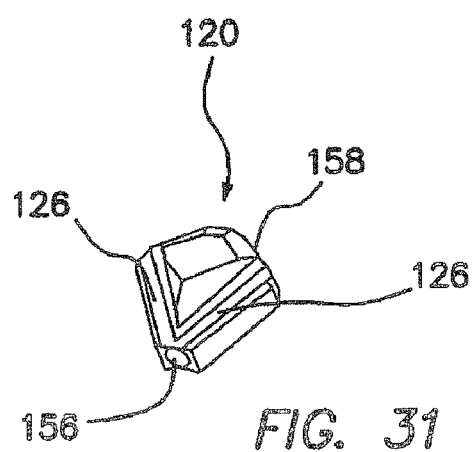
FIG. 31 is a view of the wedge of the invention.
Figure 50:
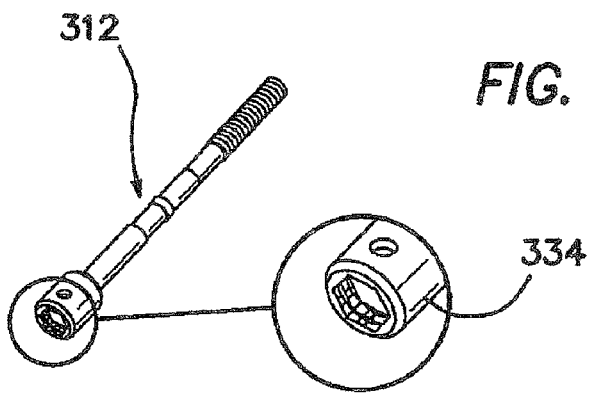
FIG. 50 is a perspective view of the deployment screw of yet another embodiment of the inventive implant.

The arms 124 include a few key design features, as particularly shown in FIGS. 29 and 30. Fins 146 on the top provide torsional strength for the wedge 120 to arm 124 junction. They also allow easier insertion into the femoral tunnel when inserting into a femoral tunnel that is drilled off-axis from the tibial tunnel. The portion of the arm 24 that engages with the bone has a tapered edge 148 which allows for ease of bone displacement during deployment. The support rib 150 along the length of the arm 124 is also tapered for ease of bone displacement and provides structural support during axial loading. The torsion pins 152 engage with a torsion hole 154 to provide additional torsional strength while inserting into the femoral tunnel.

As in the prior embodiment, the wedge 120 is threaded with a female quad lead thread 156 that matches the complementary threads 132 on the deployment screw 112. The track posts 128 on the arms 124 engage with the wedge track 126 to provide torsional strength through deployment. A tapered nose 158 allows easier off-axis insertion into the femoral tunnel.

FIG. 32 is a table similar to that of FIG. 17, presenting data generated by the inventors which indicates that pull-out forces for the implant 110 were significantly higher than those of a predicate device, the RCI interference screw available from Smith & Nephew.

Still another embodiment of the inventive implant is illustrated in FIGS. 33-54, wherein like elements to those of the prior embodiments are identified by like reference numerals, preceded by the numeral 2. This embodiment 210 utilizes the cortical bone for fixation in combination with tendon-to-bone compression. In this version of the invention, the deployment screw 212 is offset to one side of the implant 210, for the purpose of permitting easier passing of tendon through the orifice. This implant deploys in two steps. The deployment screw 212 is rotated clockwise as an arm 78 and wedge 220 slide together across tapered faces 80 (FIGS. 46) and 82 (FIG. 48) until they lock together with their respective cortical locks 84, 86. The wedge 220 and the arm 78 lock into place by filling a majority of the cross section of the femoral tunnel. Thus, the implant is free to move in the femoral tunnel, allowing tactile feedback to ensure engagement of a cortical tab 88 with the cortex.

The screw is then rotated so that it is advanced the remainder of the way, and the compression wedge 90 engages with the compression pads, thereby pressing the tendon against the bone tunnel wall. A track 92, 94 in the compression pads 214, 216 and compression wedge 90 prevents the compression wedge from 20 engaging unevenly. A progression of deployment of the implant 210 is illustrated in FIGS. 35-42. FIGS. 43-50 illustrate various components of the embodiment. In the undeployed state, the arm is engaged with the wedge with the arm's track posts 228 engaging with a T-bar 96 of the wedge 220. This prevents the arm 78 from moving during insertion. Also, to prevent the wedge 220 from rotating during deployment, the track post 228 is inserted into a torsion slot 100.

Figure 51:
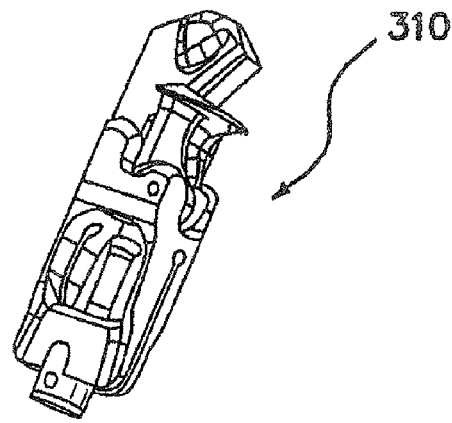
Figure 52:
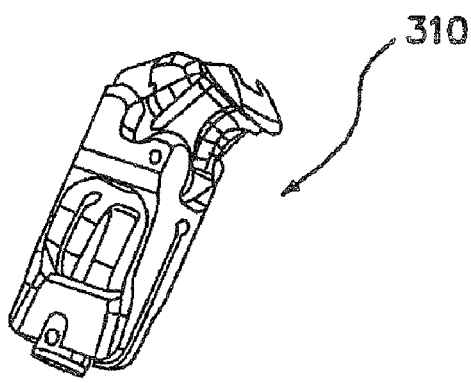
Figure 53:
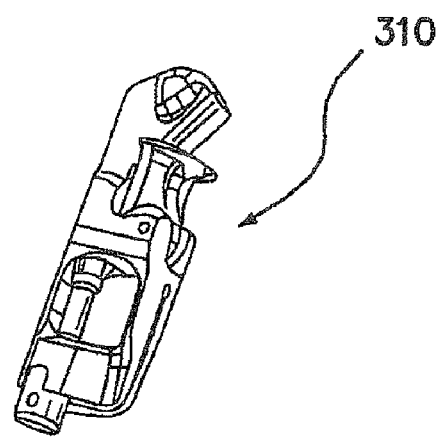
Figure 54:
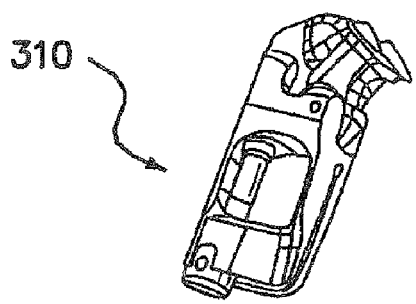

Modified cortical fixation implant designs are illustrated in FIGS. 51-54. FIGS. 51 and 52 illustrate a modified wedge and only one arm which allows engagement with the cortical bone. FIGS. 53 and 54 illustrate the same embodiments as in FIGS. 51 and 52, wherein the screw is to one side of the implant.

Figure 55:
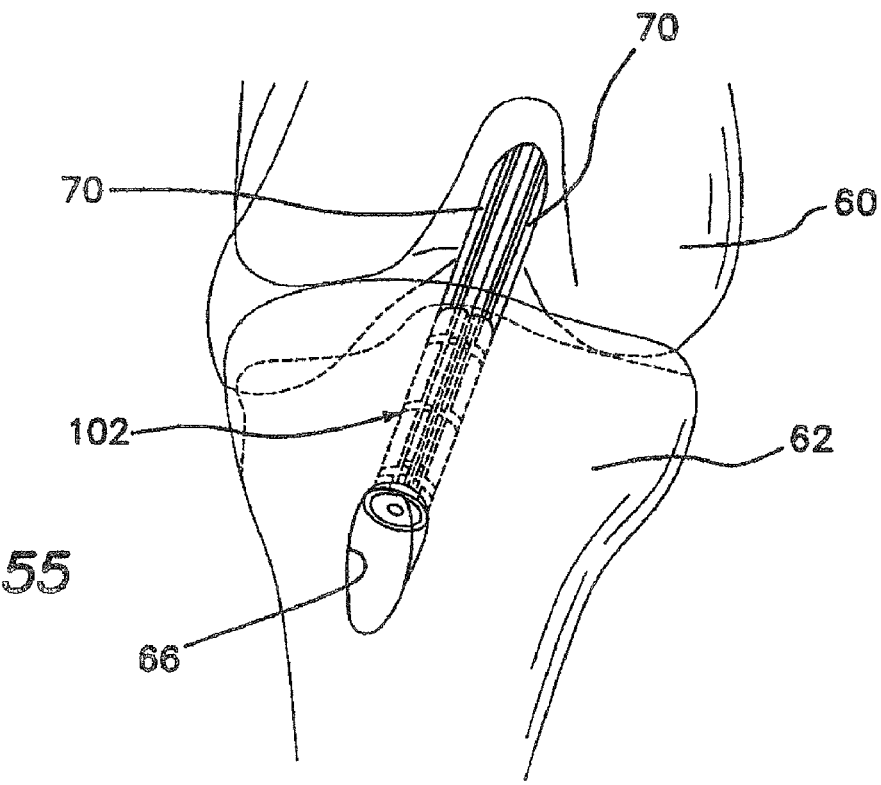
FIG. 55 is a view of the femur and tibia of a patient's leg, showing a substantially completed ACL repair.

FIG. 55 has been incorporated into this application to illustrate a substantially completed ACL repair procedure. FIGS. 8 and 9, as well as FIGS. 24 and 25 and FIGS. 41 and 42, illustrate the installation of the femoral anchor of the present invention, in various embodiments. However, as one skilled in the art would understand, to complete the repair procedure further steps are necessary. Once the femoral anchor has been deployed and installed, as previously described, the anchored tendons 70 extend proximally from the femoral tunnel through the tibial tunnel and out through tibial aperture 66. To complete the procedure, a tibial anchor 102 is preferably installed, to anchor the tendon bundles in place, as shown in FIG. 55. Once this anchor is in place, the proximal ends of the tendon bundles are trimmed to complete the procedure. This portion of the ACL reconstruction procedure is fully explained in co-pending U.S. application Ser. No. 11/725,981, which has already been fully and expressly incorporated by reference herein. Any suitable tibial anchor 102 may be used in conjunction with femoral anchors of the type disclosed in this application, but the tibial anchors shown and described in the '981 patent application are presently preferred.

Accordingly, although exemplary embodiments of the invention has been 20 shown and described, it is to be understood that all the terms used herein are descriptive rather than limiting, and that many changes, modifications, and substitutions may be made by one having ordinary skill in the art without departing from the spirit and scope of the invention.

What is claimed is:

1. A method of making an orthopedic repair by fixing a soft tissue graft to bone, comprising:
   placing a soft tissue graft on an implant;
   disposing said implant within a bone tunnel at a desired location, such that a plurality of ends of the soft tissue graft extend from said implant in a proximal direction through said bone tunnel;
   deploying a first member on a body of said implant outwardly so that portions of said first member engage adjacent bone to secure said implant in place at the desired location; and
   deploying a second member on the body of said implant outwardly so that portions of the second member engage portions of the plurality of ends of the soft tissue graft and push the soft tissue graft ends into contact with adjacent bone;
   wherein the step of deploying the first member is performed using a threaded distal end of a deployment screw which extends axially through the body, wherein the threaded distal end of the deployment screw is engaged with complementary threads on a wedge, the deployment step comprising rotating the deployment screw, thereby causing the threaded engagement between the deployment screw and the wedge to move the wedge, the movement of the wedge causing the first member to deploy outwardly; and
   wherein the step of deploying the second member is performed using a deployment screw which is rotated to move axially distally to perform said step, the deployment screw comprising an enlarged head on a proximal end thereof, the enlarged head engaging the second member to deploy it outwardly.

2. The method as recited in claim 1, wherein said bone tunnel is disposed within the femur of a patient.

3. The method as recited in claim 1, wherein the second member comprises at least one compression pad which actively compresses the soft tissue against bone defining the bone tunnel.

4. The method as recited in claim 1, wherein the first member comprises at least one arm having a tapered edge for engaging and penetrating bone.

5. The method as recited in claim 1, wherein the second member deploying step occurs before the first member deploying step.

6. The method as recited in claim 1, wherein the first member deployment step comprises moving the wedge proximally in an axial direction.

7. The method as recited in claim 1, wherein the wedge comprises a tapered construction.

8. A method of making an orthopedic repair by fixing a soft tissue graft to bone, comprising:
   drilling a bone tunnel through the tibia and partially through the femur, thereby creating a tibial tunnel and a connecting femoral tunnel;
   placing a soft tissue graft on an implant having a body;
   inserting the implant distally through a tibial inlet aperture and through the tibial tunnel, into the femoral tunnel distally of a femoral aperture, such that a plurality of ends of the soft tissue graft extend from said implant in a proximal direction through said bone tunnel;
   deploying a first member on the body of said implant outwardly so that portions of said first member engage adjacent bone to secure said implant in place at the desired location;
   deploying a second member on the body of said implant outwardly so that portions of the second member engage portions of the plurality of ends of the soft tissue graft and push the soft tissue graft ends into contact with adjacent bone;
   wherein the step of deploying the first member is performed using a threaded distal end of a deployment screw which extends axially through the body, wherein the threaded distal end of the deployment screw is engaged with complementary threads on a wedge, the deployment step comprising rotating the deployment screw, thereby causing the threaded engagement between the deployment screw and the wedge to move the wedge, the movement of the wedge causing the first member to deploy outwardly; and
   wherein the step of deploying the second member is performed using a deployment screw which is rotated to move axially distally to perform said step, the deployment screw comprising an enlarged head on a proximal end thereof, the enlarged head engaging the second member to deploy it outwardly.

9. The method as recited in claim 8, wherein the second member comprises at least one compression pad which actively compresses the soft tissue against bone defining the bone tunnel.

10. The method as recited in claim 9, wherein the at least one compression pad comprises two compression pads.

11. The method as recited in claim 8, wherein the first member comprises at least one arm having a tapered edge for engaging and penetrating bone.

12. The method as recited in claim 8, wherein the second member deploying step occurs before the first member deploying step.

13. The method as recited in claim 8, wherein the first member deployment step comprises moving the wedge proximally in an axial direction.

14. The method as recited in claim 8, wherein the wedge comprises a tapered construction.

15. A method of making an orthopedic repair by fixing a soft tissue graft to bone, comprising:
   placing a soft tissue graft on an implant having a body;
   disposing said implant within a bone tunnel at a desired location, such that a plurality of ends of the soft tissue graft extend from said implant in a proximal direction through said bone tunnel;
   advancing a deployment screw axially in a distal direction through the body of the implant;
   deploying at least one compression pad disposed on the implant body in an outward direction, using an enlarged head on a proximal end of the deployment screw, so that the at least one compression pad engages and compresses portions of the ends of the soft tissue graft into contact with adjacent bone; and
   deploying at least one arm, disposed on the implant body distally of the at least one compression pad, outwardly so that an end of the at least one arm engages and penetrates adjacent bone to secure said implant in place at the desired location; and
   wherein the step of deploying the at least one arm is performed using a threaded distal end of the deployment screw, wherein the threaded distal end of the deployment screw is engaged with complementary threads on a wedge, the advancement of the deployment screw causing the threaded engagement between the deployment screw and the wedge to move the wedge, and the movement of the wedge causing the first member to deploy outwardly.

* * * * *